US00PP23736P3

(12) United States Plant Patent
Nielsen

(10) Patent No.: US PP23,736 P3
(45) Date of Patent: Jul. 9, 2013

(54) ***OSTEOSPERMUM* PLANT NAMED 'DAOSSEKSTEN'**

(50) Latin Name: *Osteospermum ecklonis*
Varietal Denomination: DAOSSEKSTEN

(75) Inventor: Rune Harboe Nielsen, Odense N (DK)

(73) Assignee: Dalina APS, Odense N (DK)

( * ) Notice: Subject to any disclaimer, the term of this patent is extended or adjusted under 35 U.S.C. 154(b) by 126 days.

(21) Appl. No.: 13/064,539

(22) Filed: Mar. 30, 2011

(65) Prior Publication Data

US 2012/0255082 P1 Oct. 4, 2012

(51) Int. Cl.
*A01H 5/00* (2006.01)

(52) U.S. Cl.
USPC ..... Plt./360

(58) Field of Classification Search
USPC ..... Plt./360
See application file for complete search history.

(56) References Cited

PUBLICATIONS

Printout of application information from Community Plant Variety Office (CPVO) website for corresponding CPVO application No. 2010/0798 filed Apr. 6, 2010 (1 page) (http://www.cpvoextranet.cpvo.europa.eu).

Printout of application information from Canadian Food Inspection Agency—Plant Varieties Journal No. 76 (Jul. 2010) for corresponding Canadian Plant Breeders' Rights application No. 10-6961 filed May 3, 2010 (1 page) (http://www.inspection.gc.ca/english/plaveg/pbrpov/joubule.shtml).

*Primary Examiner* — June Hwu
(74) *Attorney, Agent, or Firm* — Foley & Lardner LLP

(57) ABSTRACT

A new distinct cultivar of *Osteospermum* plant named 'DAOSSEKSTEN', characterized by being a compact cultivar, with globular upright to spreading shape; very well branching (8-14 per plant) with stiff and strong lateral stems and small thick leaves; color of leaves green RHS 139A (upper side) and green RHS 137B (underside); ray florets with orange color (RHS 26A) on upper side; and disc florets that appear grayed brown (RHS N199A).

6 Drawing Sheets

Latin name of the genus and species of the claimed plant: *Osteospermum ecklonis*.

Variety denomination: 'DAOSSEKSTEN'.

BACKGROUND OF THE INVENTION

The present invention relates to a new and distinct cultivar of *Osteospermum* plant, botanically known as *Osteospermum ecklonis* (DC) T. Norl., commonly known as Cape Daisy and and hereinafter referred to by the cultivar name 'DAOSSEKSTEN'.

The new *Osteospermum* cultivar is a product of a planned breeding program conducted by the inventor, Rune Nielsen, in Stige, Denmark. The objective of the breeding program is to develop a new *Osteospermum* cultivar with good garden performance, well branching growth, continuous flowering and an attractive inflorescence color.

The new *Ostospermum* cultivar originated from a cross made in a controlled breeding program by the inventor in 2007, in Stige, Denmark. The female or seed parent is a yellow colored *Osteospermum* cultivar Sunny® 'Shiela' (patented, U.S. Plant Pat. No. 18,066). The male or pollen parent is an orange colored *Osteospermum* 'DAOSTOLV' (Plant Breeder's Right, CPVO No. 2008/0604).

Asexual reproduction of the new *Osteospermum* cultivar by terminal cuttings was first performed in November, 2008 in Stige, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DAOSSEKSTEN', which in combination distinguish this *Osteospermum* as a new and distinct cultivar:

1. Compact cultivar, with globular upright to spreading shape;
2. Very well branching (8-14 per plant) with stiff and strong lateral stems and small thick leaves. Color of leaves Green RHS 139A (upper side) Green RHS 137B (underside);
3. Ray florets with Orange color (RHS 26A) on upper side; and
4. Disc florets that appear grayed brown (RHS N199A).

Plants of the new *Osteospermum* 'DAOSSEKSTEN' differ from plants of the parents, Sunny® 'Shiela' (U.S. Plant Pat. No. 18,066) and 'DAOSTOLV' (CPVO No. 2008/0604) in the traits described in Table 1.

TABLE 1

Comparison with Parental Varieties

| Trait | New Cultivar 'DAOSSEKSTEN' | Female Parent Sunny ® 'Shiela' (U.S Plant Pat. No. 18,066) | Male Parent 'DAOSTOLV' (CPVO No. 2008/0604) |
|---|---|---|---|
| Plant Size | | | |
| Height: | About 13 cm. | About 16 cm. | About 17 cm. |
| Diameter: | About 16 cm. | About 18 cm. | About 20 cm. |

TABLE 1-continued

| Comparison with Parental Varieties | | | |
|---|---|---|---|
| Trait | New Cultivar 'DAOSSEKSTEN' | Female Parent Sunny ® 'Shiela' (U.S Plant Pat. No. 18,066) | Male Parent 'DAOSTOLV' (CPVO No. 2008/0604) |
| Overall Plant Shape: | Globular upright to spreading, with very good basal and axillary branching. | Upright to spreading, with basal branching. | Upright to spreading, with basal branching. |
| Stem | | | |
| Length: | About 6 cm. | About 7 cm. | About 7 cm |
| Diameter: | About 5 mm | About 5 mm. | About 6 mm. |
| Strength: | Stiff and strong. | Medium strong. | Stiff and strong. |
| Color: | RHS 144A (yellow-green). | RHS 144C (yellow-green). | RHS 144A (yellow-green). |
| Number of Inflorescence heads per Plant: | About 35. | About 20. | About 25. |
| Flower Size Diameter: | About 6.5-7 cm. | About 7-8 cm. | About 8.5 cm. |
| Mature Petal Color (upper surface): | RHS 26A (orange). | RHS 30A (orange-red), near base RHS N74B (red-purple). | N167A (greyed-orange) with spots of 21C (yellow-orange). |
| Color of disc florets (as they appear when sitting in composite flower head). | RHS N199A (greyed-brown). | RHS 59A (red-purple). | RHS N200A (brown). |

Of the many commercial cultivars known to the present inventor, the most similar in comparison to the new *Osteospermum* 'DAOSSEKSTEN' is the *Osteospermum* cultivar 'Cape Daisy® Terracotta', in the characteristics described in Table 2.

TABLE 2

| Comparison with Comparison Variety | | |
|---|---|---|
| Trait | New Cultivar 'DAOSSEKSTEN' | Comparison Cultivar 'Cape Daisy ® Terracotta' |
| Plant Size | | |
| Height: | About 13 cm. | About 14 cm. |
| Diameter: | About 16 cm. | About 17 cm. |
| Overall Plant Shape: | Globular upright to spreading, with very good basal and axillary branching. | Upright to spreading, with basal branching. |
| Stem | | |
| Length: | About 6 cm. | About 3 cm. |
| Diameter: | About 5 mm | About 5 mm. |
| Strength: | Stiff and strong. | Medium strong. |
| Color: | RHS 144A (yellow-green). | RHS 144B (yellow-green). |
| Number of Inflorescence heads per Plant: | About 35. | About 25. |
| Flower Size Diameter: | About 6.5-7 cm. | About 8 cm. |
| Mature Petal Color (upper surface): | RHS 26A (orange). | RHS N25D (orange) |
| Color of disc florets (as they appear when sitting in composite flower head). | RHS N199A (greyed-brown). | RHS 200A (brown) |

BRIEF DESCRIPTION OF THE PHOTOGRAPHS

The accompanying photographs illustrate the overall appearance of the new *Osteospermum* 'DAOSSEKSTEN' showing the colors as true as is reasonably possible with colored reproductions of this type. Colors in the photographs may differ slightly from the color value cited in the detailed botanical description, which accurately describe the color of 'DAOSSEKSTEN'.

Figure 1:
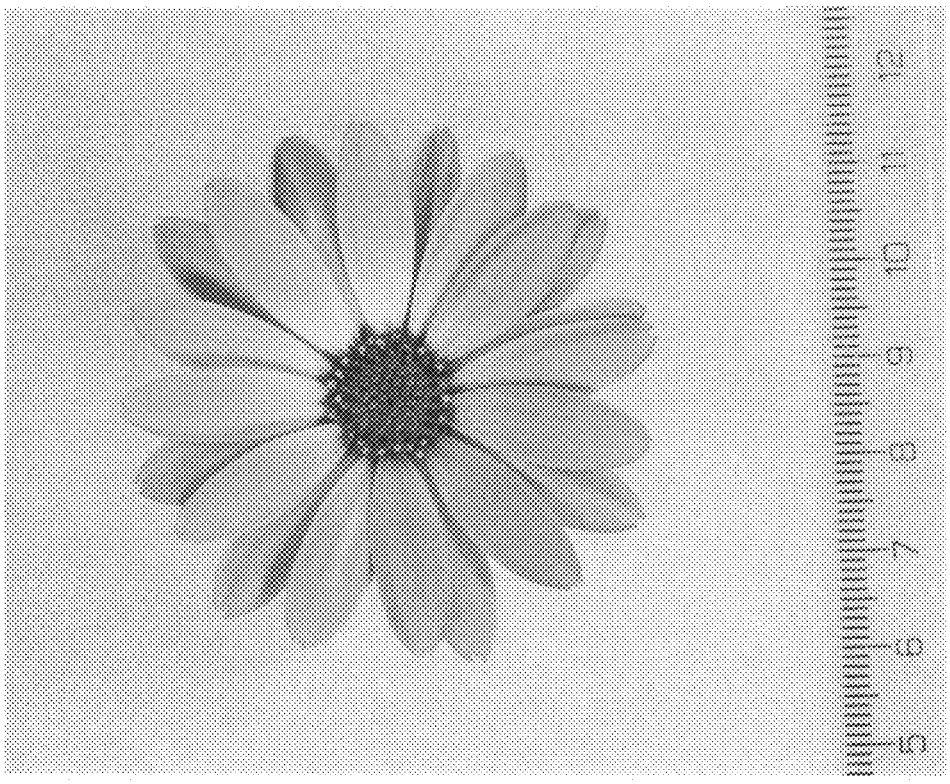
FIG. 1 shows a close-up view of the composite flower head from 'DAOSSEKSTEN'.
Figure 2:
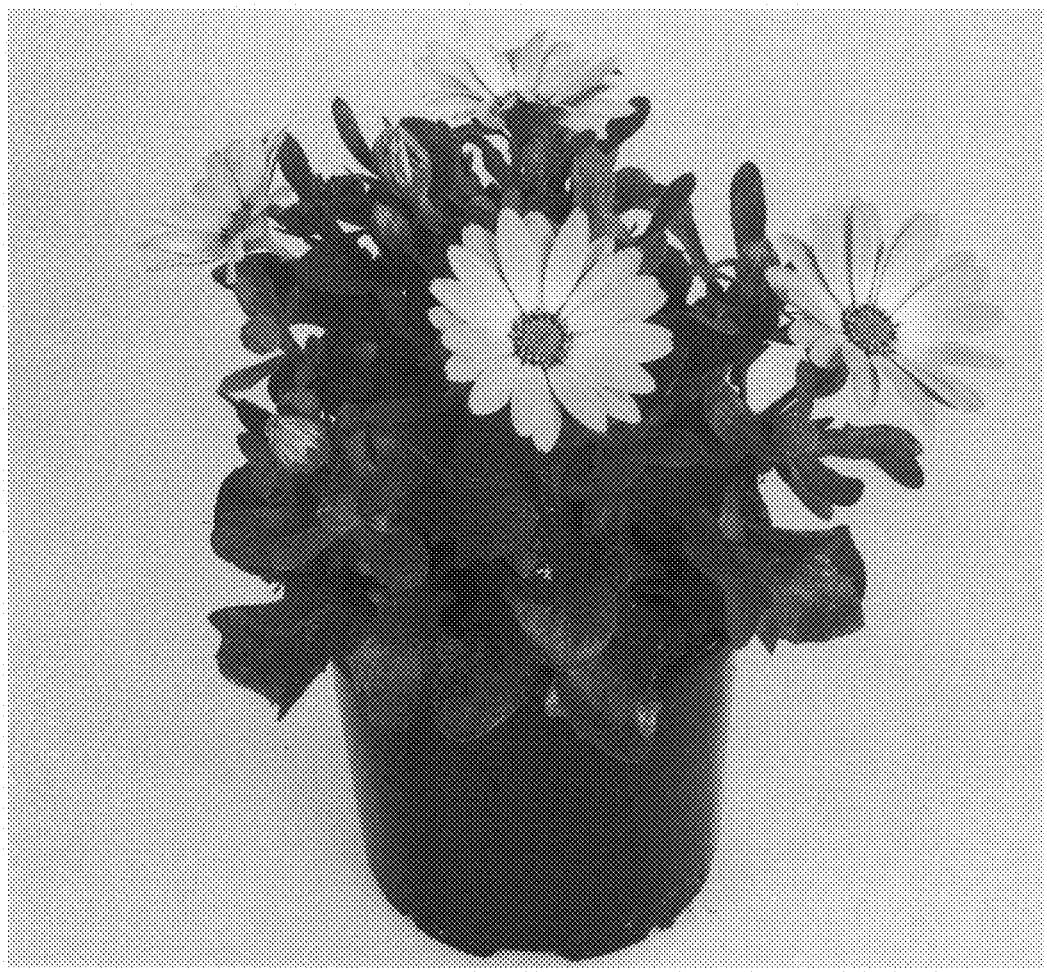
FIG. 2 shows a side view perspective of a typical flowering plant of 'DAOSSEKSTEN' in a 11 cm pot, at 12 weeks of age after planting.
Figure 3:
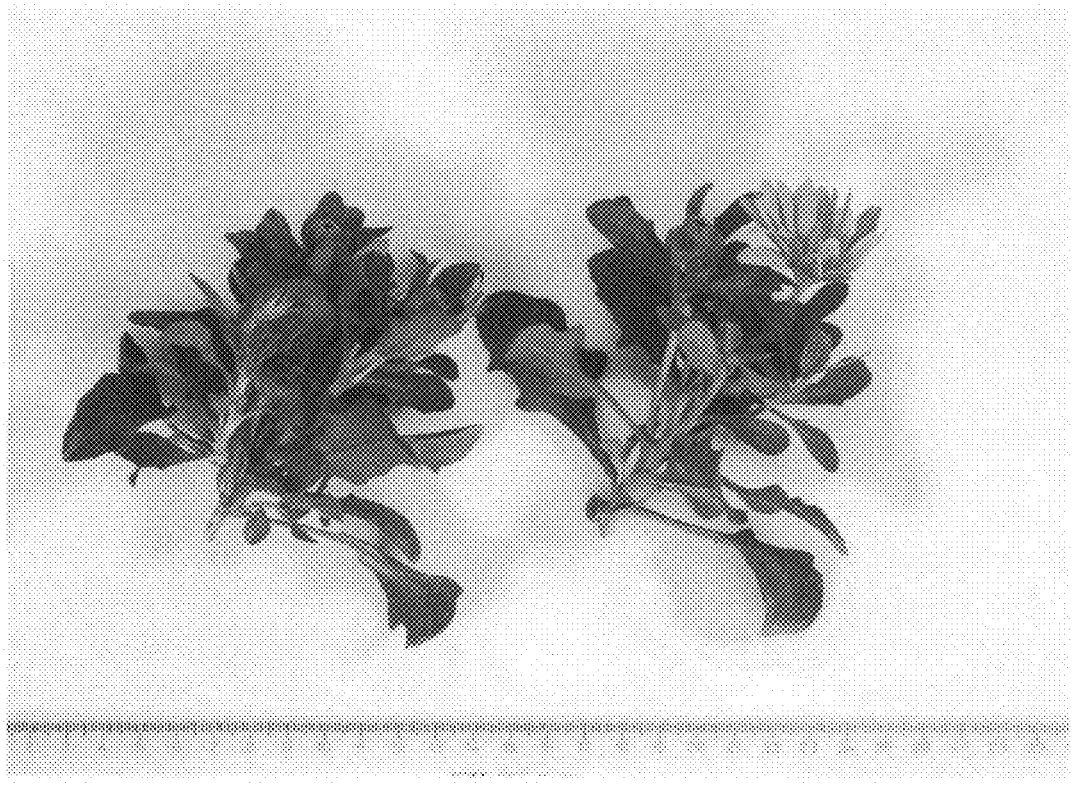
FIG. 3 shows a close-up view of the typical lateral stems with leaves and buds of 'DAOSSEKSTEN'.
Figure 4:
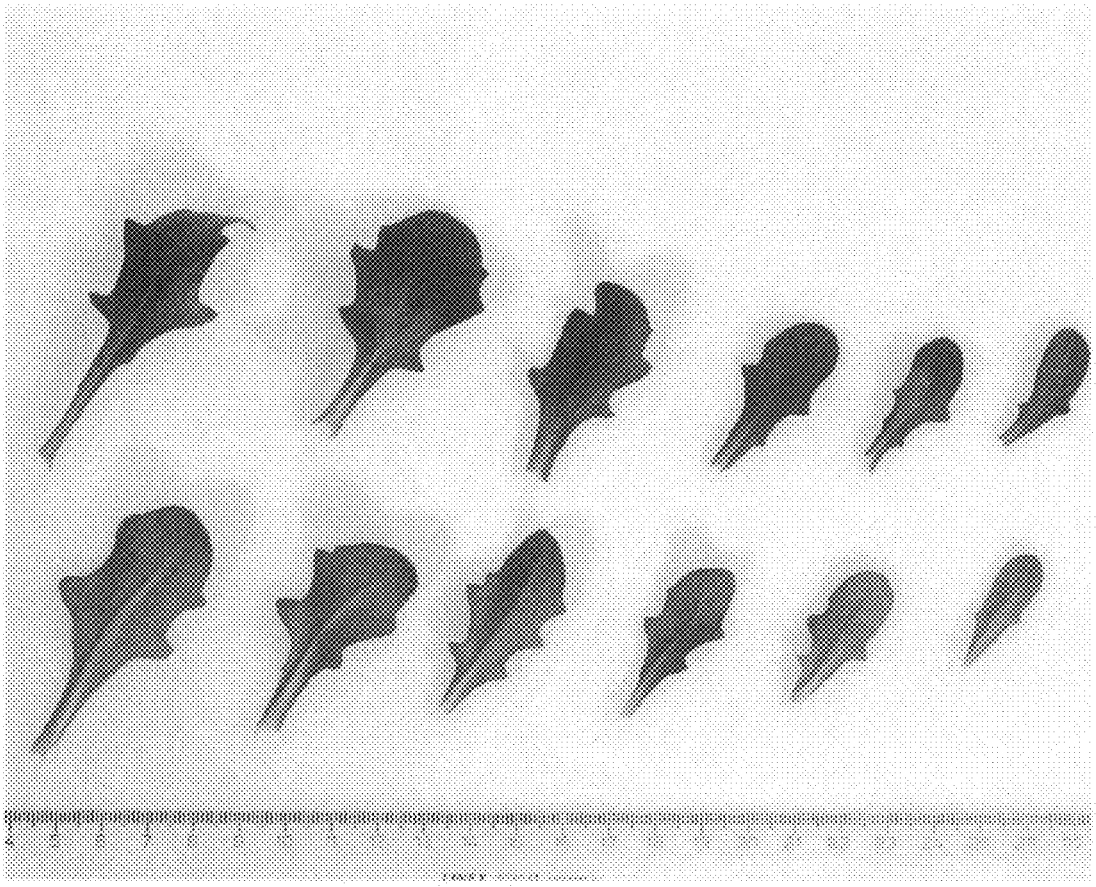
FIG. 4 shows a close-up view of the different leaf sizes of 'DAOSSEKSTEN'.
Figure 5:
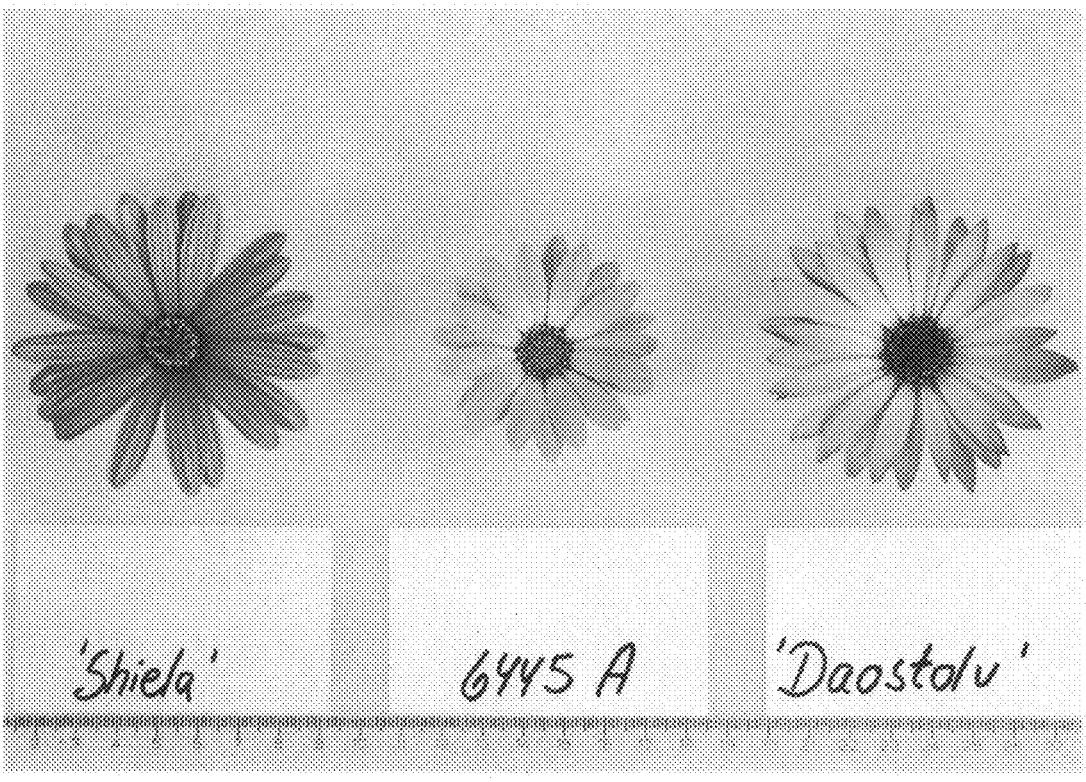

FIG. 5 shows a comparison between female parent Sunny® Shiela (U.S. Plant Pat. No. 18,066), male parent 'DAOSTOLV' (CPVO No. 2008/0604) and 'DAOSSEKSTEN', (Breeders reference: 6445A).

Figure 6:
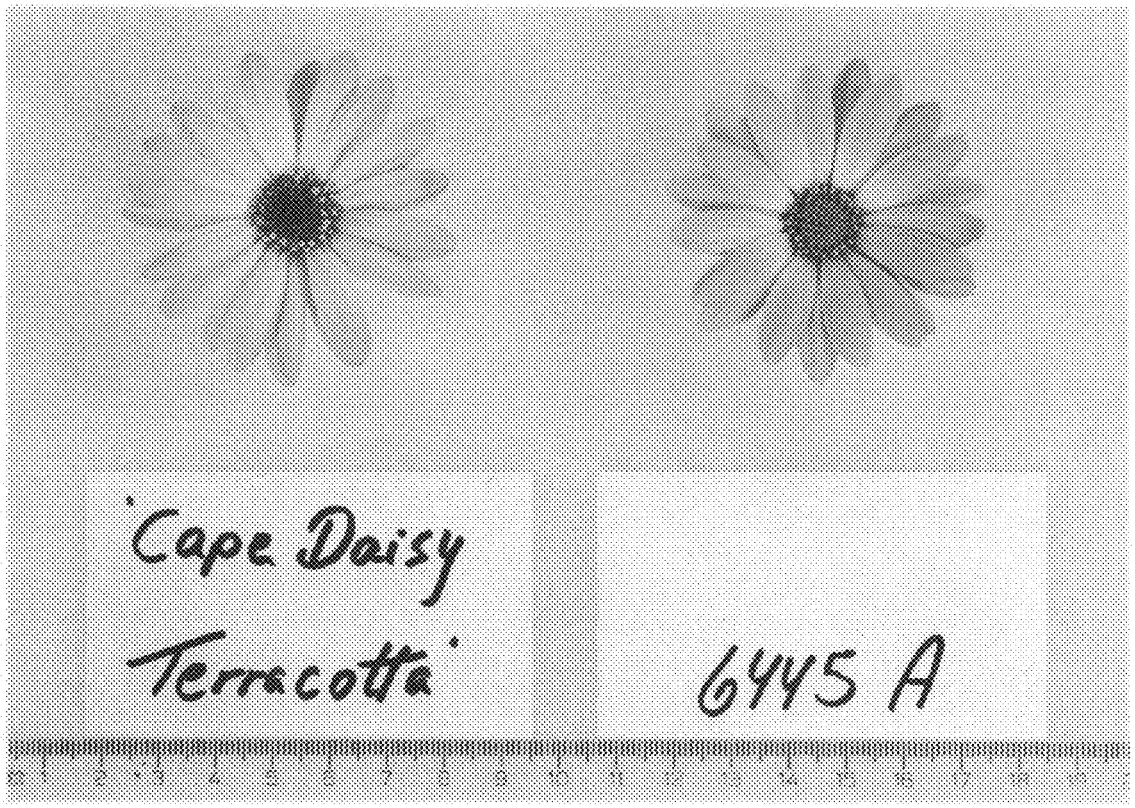

FIG. 6 shows a comparison between 'CAPE DAISY® Terracotta' and 'DAOSSEKSTEN', (Breeders reference: 6445A).

DETAILED BOTANICAL DESCRIPTION

The new *Osteospermum* 'DAOSSEKSTEN' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Osteospermum* 'DAOSSEKSTEN' as grown in a glasshouse, equipped with heat, assimilation light and ebb/flood watering system in Odense, Denmark, under conditions which closely approximate those generally used in commercial practice. The plants was grown in 14° C., with a venting temperature on 16° C. Assimilation light was given when natural daylight was below 3000 lux and the day length was extended to 16 hours. The EC levels in the soil, was kept at about 2.5-3.5 and pH around 6.0 during the production. Plant growth was regulated 3 times during the production period, using 3‰ Cycocel (chlormequat-chloride) as a drench (80-100 ml/pot).

Color references are made to The Royal Horticultural Society Colour Chart (R.H.S.), Colour Chart 2001 edition, Color values were taken under March daylight conditions at approximately 10:00-14:00 in Stige, Denmark. The age of the 'DAOSSEKSTEN' plants described is 12 weeks from potting.

Classification:

*Botanical.—Osteospermum ecklonis* (DC) Norl.

Parentage:

*Female or seed parent.—Osteospermum* cultivar designated Sunny® 'Shiela' (U.S. Plant Pat. No. 18,066).

*Male or pollen parent.—Osteospermum* variety designated 'DAOSTOLV' (CPVO No. 2008/0604).

Propagation:

*Type*.—Vegetative terminal cuttings.

*Time and temperature to initiate roots*.—About 9 to 13 days at 19 to 21° C. in tunnels in a greenhouse.

*Time and temperature to produce a rooted young plant*.—About 4 to 5 weeks at 18° (initiation period benefits from 19-21° C.).

*Rooting habit*.—Vigorous, white to grayed yellow and well branched.

Plant description:

*General appearance and form*.—Globular upright, with basal branching. Inflorescences in composite heads. Freely branching with lateral flowering branches forming at every node.

*Growth rate*.—Growing about 1 cm per week during production period.

*Plant height*.—About 12 cm to 15 cm.

*Plant width* (*spread*).—About 15 cm to 17 cm.

*Crop time to produce a mature flowering plant*.—It requires 4-5 weeks to produce a young plant in a 35 mm propagation plug. After potting 12-14 weeks are required to produce finished flowering plants in 11 cm pots.

Stem:

*Shape*.—Round.

*Length*.—About 4 cm to 6 cm.

*Diameter*.—About 3 mm to 5 mm.

*Strength*.—Stiff and strong.

*Aspect*.—Upright.

*Texture*.—Smooth and glabrous.

*Color*.—Mature: RHS 144A. Immature: RHS 144C.

Branches:

*Branching habit*.—Basal branching with very good lateral branching.

*Number of branches per plant*.—About 3-5 branches, spreading into 18-20 lateral branches.

*Length* (*including flowers*).—About 11 cm to 12 cm.

*Diameter*.—About 5 mm.

*Strength*.—Stiff and strong.

*Aspect*.—Upright to spreading.

*Texture*.—Smooth and glabrous.

*Color*.—Mature: RHS 144A. Immature: RHS 144C.

*Internode length*.—About 4 to 10 mm.

*Internode color*.—RHS 144A.

Foliage description:

*Arrangement*.—Alternate.

*Number of leaves per branch*.—About 8 to 12 per branch.

*Length*.—About 4 cm to 7 cm.

*Width*.—About 1 cm to 3 cm.

*Overall shape of leaf*.—Obovate to spatulate with 1 to 3 acuminate teeth on each side.

*Shape at apex*.—Obtuse.

*Shape at base*.—Attenuate.

*Margin*.—Dentate (1-3 lobes on each leaf).

*Texture*.—Upper surface: Pubescent with scattered short, stiff hairs. More hairs on the edges of leaf. Lower surface: Pubescent with scattered short, stiff hairs More hairs along veins and on the edges of leaf. Young leaves appear more hairy than older.

*Color of developing foliage*.—Upper surface: RHS 137A. Lower surface: RHS 137C.

*Color of mature foliage*.—Upper surface: RHS 139A. Lower surface: RHS 137B.

*Venation pattern*.—Trinerved with veins along nerves.

*Venation color*.—Upper surface: RHS 147B. Lower surface: RHS 146B.

Inflorescence description:

*Arrangement and shape*.—Tubular disc floret and flat, lanceolate ray florets in composite flower heads, developed from terminal and axillary shoots. The peduncles lift the Inflorescences 0-4 cm above the foliage. Inflorescences face upright to 70° angle from vertical.

*Natural flowering season*.—*Osteospermum* is a bedding plant, with a flowering season from early spring to late autumn. Temperatures below 20° C. will increase flowering, temperatures above 20° C. will reduce flowering.

*Time to flower*.—65 to 85 days.

*Inflorescence longevity on the plant*.—Inflorescence will maintain good color and substance for about 5-10 days; however, the longevity of individual inflorescence is highly dependent on temperature and light conditions. Inflorescence persistent.

*Quantity of inflorescences heads*.—Freely flowering; about 30-40 buds and open inflorescences per plant.

*Fragrance*.—Very discreet smell.

*Bud* (*Inflorescences head*).—Rate of opening (from showing color to fully open flower: 1 to 5 days. The rate of opening is highly dependent on temperature and light conditions. Length: About 12 mm. Diameter: About 10 mm. Shape: Semiglobose. Texture: Pubescent with small hairs. Color: RHS 144A at base to 137A at apex.

*Peduncle*.—From both terminal and axillary shoots. Length: About 3-5 cm. Diameter: About 2 mm. Angle: About 0-30° from vertical. Strength: Medium strong. Texture: Pubescent with small white hairs. Color: RHS 144A.

*Inflorescence head*.—Depth: About 10 mm. Diameter: About 7-8 cm. Disc Diameter: 12 mm. Receptacle (phoranthium) surface shape: Slightly Rounded.

*Ray florets*.—Quantity per Inflorescence head: 20-24. Length: 30 mm. Widths: 7-9 mm. Overall shape: Spatulate. Shape at apex: Acute with small clefts (usually 2) at the tip (praemorse). Shape at base: Acute. Margin: Entire, small cleft at apex. Texture: Upper surface: smooth, matt, slightly furrowed. Lower surface: smooth, matt slightly furrowed. Color upper side: RHS 26A. Color underside: Stripes of various colors; RHS 168C, RHS N170A and RHS 178B.

*Disc florets*.—Quantity per Inflorescence head: 65-75. Length: 6 mm. Diameter: 1 mm. Color RHS 163A translucent upper half, RHS 157A lower half.

*Phyllary*.—15-20. Length: 8-10 mm. Width: 1-2 mm. Overall shape: Lanceolate. Apex: Narrow Acuminate. Base: Fused. Margin: Entire. Color: RHS 137A.

Reproductive organs:

*Androecium*.—Location: Disc florets only. Stamen number: 5 fused. Stamen length: About 5 mm. Anther shape: Linear, fused. Anther length: About 2 mm. Pollen amount: Medium amount. Pollen color: RHS 14A.

*Gynoecium*.—Location: Ray and disc florets. Quantity: 1. Pistil length: About 5 mm. Stigma shape: Brush-like, cleft 1.5 mm deep. Stigma length: About 2 mm. Stigma color: RHS N192A on tip and along edges, rest N155A. Style length: About 3 mm. Style color: RHS 155A. Ovary color: RHS 145B.

Seed/fruit: Seed and fruit production has not been observed.

Disease/pest resistance: Resistance to pathogens and pests common to *Osteospermum* has not been observed.

Disease/pest susceptibility: Susceptibility to pathogens and pests common to *Osteospermum* has not been observed.

Temperature tolerance: Plants of the new *Osteospermum* have exhibited good tolerance rain, wind and drought; however, flowering may cease during hot periods (temperatures above 25° C.). Low temperature tolerance to 1° C.

What is claimed is:

1. A new and distinct cultivar of *Osteospermum* plant named 'DAOSSEKSTEN', as illustrated and described herein.

* * * * *